United States Patent [19]

Dufresne et al.

[11] Patent Number: 4,977,121

[45] Date of Patent: Dec. 11, 1990

[54] MORDENITE-CONTAINING CATALYST, ITS PREPARATION AND USE FOR ISOMERIZING CUTS OF HIGH NORMAL PARAFFIN CONTENT

[75] Inventors: Pierre Dufresne, Rueil-Malmaison; Jean-Pierre Franck, Bougival; Françis Raatz; Christine Travers, both of Rueil-Malmaison, all of France

[73] Assignee: Institut Francais du Petrole, Rueil-Malmaison, France

[21] Appl. No.: 5,806

[22] Filed: Jan. 22, 1987

[30] Foreign Application Priority Data

Jan. 22, 1986 [FR] France ............................ 86 00992

[51] Int. Cl.$^5$ ............................................. B01J 29/20
[52] U.S. Cl. ...................................... 502/66; 502/74; 502/78
[58] Field of Search .................. 502/78, 66; 585/739

[56] References Cited

U.S. PATENT DOCUMENTS

| | | | |
|---|---|---|---|
| 3,413,370 | 11/1968 | Fishel | 260/666 |
| 3,432,568 | 3/1969 | Miale | 260/676 |
| 3,475,345 | 10/1969 | Benesi | 252/455 Z |
| 3,480,539 | 11/1969 | Voorhies, Jr. et al. | 208/111 |
| 3,598,724 | 8/1971 | Mulaskey | 502/78 |
| 3,632,835 | 1/1972 | Mitsche et al. | 260/666 |
| 3,663,430 | 5/1972 | Morris | 208/111 |
| 3,751,502 | 8/1973 | Hayes et al. | 502/78 |
| 3,836,597 | 9/1974 | Sie | 260/683.65 |
| 3,842,114 | 10/1974 | Sie | 585/739 |
| 4,359,409 | 11/1982 | Den Otter | 252/455 Z |
| 4,374,296 | 2/1983 | Haag et al. | 585/739 |
| 4,400,576 | 8/1983 | Den Otter | 585/739 |
| 4,501,656 | 2/1985 | DuFrense et al. | 208/111 |

FOREIGN PATENT DOCUMENTS

| | | | |
|---|---|---|---|
| 46615 | 3/1982 | European Pat. Off. | 502/78 |
| 196965 | 10/1986 | European Pat. Off. | 502/78 |
| 2471359 | 6/1981 | France . | |

*Primary Examiner*—Carl F. Dees
*Attorney, Agent, or Firm*—Millen, White & Zelano

[57] ABSTRACT

The invention concerns a catalyst containing by weight:
(a) from 10 to 99.99% of a mordenite being in major part shaped as needles and having a Si/Al atomic ratio of about 5 to 50, a benzene adsorption capacity of more than 5% by weight with respect to the dry mordenite weight, a volume V of a unit cell from 2.73 to 2,78 nm$^3$, a sodium content by weight lower than 0.2% and adsorbing molecules of a kinetic diameter larger than about $6.6 \times 10^{-10}$ m,
(b) from 0 to 89.99% of a matrix,
(c) from 0.005 to 15% of at least one metal from group VIII, and
(d) from 0.005 to 10% of at least one metal from group IV A.

The catalyst is used for hydroisomerizing cuts containing a high proportion of normal paraffins having 4, 5, 6 or 7 carbon atoms per molecule to obtain with a good conversion and selectivity a mixture containing a high proportion of isoparaffins.

6 Claims, No Drawings

MORDENITE-CONTAINING CATALYST, ITS PREPARATION AND USE FOR ISOMERIZING CUTS OF HIGH NORMAL PARAFFIN CONTENT

The present invention concerns a catalyst comprising a particular mordenite, at least one metal from group IVA of the periodic classification of elements (Handbook of Chemistry and Physics, 6th edition 1980-81) and at least one metal from group VIII of said classification, with optionally a matrix or binder.

The present invention also concerns processes for preparing these catalysts and their use, in particular for hydroisomerizing cuts containing a high proportion of normal paraffins having 4, 5, 6 or 7 carbon atoms per molecule.

BACKGROUND OF THE INVENTION

The isomerization of normal paraffins of low molecular weight is of considerable interest in the petroleum industry, in view of the very high octane number of isoparaffins.

The conversion of $C_4$-$C_7$ and mainly $C_5$-$C_6$ n-paraffins to isoparaffins has the high advantage of producing a motor fuel of high octane number. This process can be used advantageously for improving light gasoline cuts and particularly straight-run head fractions.

Three different types of isomerization processes exist:
the low temperature processes (at about 20°-130° C.) using a Friedel and Crafts catalyst such as aluminum chloride,
The "medium" temperature processes (at about 150° C.) using as catalyst a supported metal such as platinum on halogenated alumina,
the high temperature processes (at 250° C. and more), using zeolite carriers associated with a group VIII hydrogenating metal.

Irrespective of the type of catalyst used, the isomerization reaction is generally accompanied with a more or less substantial cracking reaction, depending on the catalyst and on the operating conditions.

The "high temperature" processes have been disclosed in a large number of patents within the last twenty years. Most of them use a more or less extensively modified zeolite, particularly a mordenite, generally in acid form, with or without hydrogenation promoters.

Examples of such patents are those of SHELL Company using catalysts comprising mordenites modified by particular processes: U.S. Pat. Nos. 2,181,928, 2,272,737, 3,190,939, 3,442,794, 3,475,345, 3,836,597, 3,842,114, 4,359,409 and 4,400,576.

Other examples are patents to ESSO Company using partially dealuminated mordenites, such as U.S. Pat. Nos. 3,480,539, 3,506,400 and a patent to MOBIL Company, U.S. Pat. No. 3,551,353.

Two modes of metal deposition are considered:
deposition of metal on the modified zeolite, disclosed in most of the above-mentioned patents,
deposition of the one or more metals on an inert binder, for example alumina, and physical admixture with the zeolite in protonic form (patents to MOBIL Company U.S. Pat. Nos. 3,432,568 and 4,374,926 and patent to UOP Company: U.S. Pat. No. 3,632,835).

Particular treatments of the zeolite such as fluorine introduction were also disclosed in U.S. Pat. Nos. 3,932,554 and 3,413,370.

Mordenite is characterized by a Si/Al atomic ratio usually ranging from 4 to 6; its crystalline structure is constituted by a linking of $SiO_4$ and $AlO_4$ tetrahedrons, generating two types of channels: channels with dodecagonal opening (contour with 12 oxygens) and channels with octogonal opening (contour with 8 oxygens).

Two types of mordenite exist which are distinguished from each other by their adsorption properties: the so-called wide-pore form, always synthetic, which adsorbs molecules such as benzene (kinetic diameter = $6.6 \times 10^{-10}$ m) and the so-called small-pore form, natural or synthetic, which only adsorbs molecules of a kinetic diameter lower than about $4.4 \times 10^{-10}$ m. These mordenites are also distinguishable by their morphological differences: needles for the so-called small-pore mordenite, spherulites for the so-called wide-pore mordenite, and structural differences: presence or absence of defects. In the above-mentioned literature, the so-called wide-pore variety is used.

SUMMARY OF THE INVENTION

The catalyst according to the present invention, which is particularly selective for hydroisomerizing cuts containing a high proportion of normal paraffins having 4 to 7 carbon atoms per molecule, comprises a mordenite of particular structure prepared from a so-called small-pore mordenite under such conditions that the resultant mordenite has the capacity to adsorb the benzene molecule (kinetic diameter: $6.6 \times 10^{-10}$ m) while keeping, in major part, the morphology of the initial mordenite.

The particular manufacturing process for producing the mordenite used for the catalyst according to the invention has been disclosed by the applicant in the U.S. patent application filed on Apr. 7, 1986 under Ser. No. 848 547 (and now abandoned), corresponding to the European patent application EP-A-196 965 published on Oct. 8, 1986.

The description of the preaparation of the mordenite used for the catalyst according to the invention is hereinafter incorporated by reference.

More precisely, the catalyst according to the present invention contains by weight:

(a) from 10 to 99.99%, preferably from 35 to 85%, advantageously from 40 to 85% and more preferably from 60 to 85% of a mordenite adsorbing molecules of a kinetic diameter greater than $6.6 \times 10^{-10}$ m, having a Si/Al atomic ratio from about 5 to 50 and preferably from about 5 to 30, a sodium content by weight lower than 0.2% and preferably lower than 0.1% of the weight of dry mordenite, a unit cell volume V of 2.73-2.78 cubic nanometers ($nm^3$) and preferably from 2.74 to 2.77 $nm^3$, a benzene adsorption capacity higher than 5% and preferably higher than 8% of the dry mordenite weight, a particular morphology consisting mainly of needles.

The needles have usually a length from 2 to 20 $\mu m$, more particularly from 3 to 10 $\mu m$ and preferably an average length of 5 $\mu m$. The hexagonal faces of said needles generally have a length from 0.5 to 4 $\mu m$ and more particularly from 0.5 to 3 $\mu m$ and a "height" from 0.1 to 2 $\mu m$, more particularly from 0.2 to 1 $\mu m$; preferably the major part of the hexagonal faces (i.e. at least 50% of the faces) have a length of about 1 $\mu m$ and a "height" of about 0.3 $\mu m$.

(b) from 0 to 89.99%, preferably from 15 to 60%, advantageously from 15 to 55%, and more preferably from 15 to 35% of a matrix or binder selected from the group consisting of alumina, silica, magnesia, zirconia, natural clays and mixtures thereof, such for example as silica-alumina; the matrix will preferably be alumina or a mixture containing a major proportion of alumina, (c) from 0.005 to 15%, preferably from 0.05 to 10%, of at least one metal from group VIII of the periodic classification of elements, the preferred metals being platinum, palladium and nickel and the metal content being preferably from 0.05 to 1%, more preferably from 0.1 to 0.6% when palladium or platinum are concerned and from 0.1 to 10%, more preferably from 0.2 to 5%, when nickel is concerned, (d) from 0.005 to 10%, preferably from 0.01 to 5% and more preferably from 0.1 to 4% of at least one metal from group IVA of the periodic classification of elements such as tin, germanium or lead, preferably tin, the sum of the percentages by weight of all the elements contained in the catalyst being always 100%.

The atomic ratio between the one or more group IVA metals and the one or more group VIII metals (IVA/VIII) is usually from 0.25:1 to 20:1 and preferably from 0.4:1 to 10:1.

For the purpose of the present invention, a mordenite mainly formed of needles is a mordenite containing at least 50%, preferably at least 75% and more preferably at least 85% by weight of mordenite of these particular needles (morphology). The mordenite used in the catalyst according to the present invention is manufactured from a so-called small-pore mordenite, for example a mordenite of the trade having a sodium content by weight generally from 4 to 6.5% of the weight of dry mordenite, whose Si/Al atomic ratio is generally from 4.5 to 6.5 and whose unit cell volume is generally from 2.77 to 2.80 nm$^3$. This mordenite only adsorbs molecules of a kinetic diameter smaller than about $4.4 \times 10^{-10}$ m.

The different characteristics are measured by the following methods:
the total Si/Al atomic ratios are determined by X fluorescence analysis, the sodium contents by atomic absorption,
the unit cell volume and the crystallinity are determined by X-ray diffraction, the sample preparation being similar to the operating mode of Standard ASTM D 3942 80 prescribed for faujasite,
the benzene adsorption capacity of mordenite is determined by gravimetry. The sample is previously desorbed at 300° C. under $10^{-4}$ Torr (133.32 $10^{-4}$ Pa). The adsorption is then conducted at 30° C. for 4 hours under a benzene pressure P of 28 Torr (3733 Pa), which corresponds to a P/Ps ratio of 0.25, Ps being the saturating vapor pressure at the temperature of the experiment.

The adsorbed volumes are calculated from the density of the adsorbate in liquid form at the adsorption temperature: d=0.868.

Various methods can be used to obtain a mordenite having the above-defined characteristics and particular needle morphology, from a so-called small-pore mordenite.

According to a preferred method, the so-called small-pore mordenite is subjected to the following different treatments: the sodium cations are exchanged with ammonium cations by dipping the mordenite in a solution of ionizable ammonium salt of molarity usually above 0.5, at a temperature generally ranging from 20° to 150° C. This exchange is repeated several times. The product obtained after these cation exchanges may be washed and then subjected to a thermal treatment in the presence of steam, conducted in accordance with the self steaming technique (roasting in confined atmosphere). A temperature from 300° to 800° C., preferably from 400° to 700° C., is maintained generally more than 10 minutes and preferably more than 20 minutes. The roasting atmosphere contains at least 1% and preferably at least 5% of steam. For self steaming, the atmosphere consists essentially of water and ammonia. The obtained product may be subjected to an acid treatment for extracting aluminum from the solid. This treatment may be performed by dipping the product in a strong inorganic or organic acid of normality from 0.1 to 12N, at a temperature from 20° to 150° C., and preferably from 80° to 150° C., for a time preferably longer than 10 minutes.

After this acid treatment the product may be washed, for example with acid, then with water. Another method of preparation of the mordenite according to the invention also gives a good catalyst by a different procedure.

The so-called small-pore mordenite in sodium form may be directly treated in one or more operations with an inorganic or organic acid, of normality ranging from 0.1 to 12N, at a temperature from 20° to 150° C., preferably from 80° to 150° C. The aluminum amount extracted by this acid treatment must be at least 20%, which means that the Si/Al ratio must be at least about 6.5. It is then optionally possible to complete the sodium cation exchange by treating the product with solutions of a ionizable ammonium salt. The introduction of a metal, for example a group VIII metal, is then conducted in accordance with one of the procedures described hereinafter.

Other dealumination methods may be considered such as acid etching with hydrofluoric acid, hydrochloric acid in gas phase, or the treatment with a fluorosilicate or any other method known in the art.

The catalyst according to the invention also contains a matrix or binder, at least one group VIII metal and at least one group IVA metal.

When the catalyst according to the invention must be used in reactions of n-paraffin hydroisomerization, it is preferred that the one or more group IVA and group VIII metals be present simultaneously on the matrix or simultaneously on the mordenite.

The group VIII metals present in the final catalyst may be introduced before or after the admixture with the matrix. For example it is possible to first introduce at least one group IVA metal on the matrix or on the mordenite and then, after admixture of the resultant product with the mordenite or the matrix, to introduce at least one group VIII metal in order to deposit said metal, in major part, on the carrier fraction (matrix or mordenite) whereon the group IVA metal has been introduced.

More precisely, when the catalyst comprises at least one group IVA metal and at least one group VIII metal whose major part (i.e. at least 50% and preferably at least 75% and more preferably at least 95% by weight) is introduced on the matrix, the process for preparing the catalyst according to the present invention preferably comprises the following steps of:

(a) introducing at least one group IVA metal on the matrix, (b) intimately admixing the product obtained in step (a) with mordenite having the above-defined characteristics and particular needle morphology, (c) introducing at least one group VIII metal either before step (b), during or after step (a), or after step (b), so that a major part (i.e. at least 50%, preferably at least 75% and more preferably at least 95% by weight) of said metal be deposited on said matrix.

When the catalyst comprises at least one group IVA metal and at least one group VIII metal, a major part of which is introduced on the mordenite, the process for preparing the catalyst according to the present invention preferably comprises the following steps of:
(a) introducing at least one group IVA metal on a mordenite having the above-defined characteristics and particular needle morphology,
(b) intimately admixing the product obtained in step (a) with the matrix,
(c) introducing at least one group VIII metal either before step (b), during or after step (a), or after step (b), so that a major part (i.e. at least 50%, preferably at least 75% and more preferably at least 95% by weight) of said metal be deposited on the mordenite.

When the metals are introduced on the matrix or binder, the group IVA metal may be incorporated to said matrix by any known method of the art leading to a homogeneous distribution of the metal within said matrix, for example by coprecipitation, cogelation or impregnation. The group VIII metal may be introduced simultaneously, for example by coimpregnation, but it is generally preferred to introduce it separately after introduction of the group IVA metal which is then performed by means of a salt, by comixing or dry impregnation of the matrix or even by coprecipitation; the group IVA metal may also be introduced by means of organometallic compounds of said metal in organic medium.

When the matrix is alumina, the suitable salt of group IVA metal may be directly added to the alumina hydrosol; after gelation and thermal treatments, an intimate combination of said metal with alumina is obtained. It is also possible to impregnate the alumina matrix with a decomposable soluble salt of group IVA metal, the solvent being generally water. The preferred salts of group IVA metals are chlorides, nitrates, sulfates, acetates and amminated complexes. Other compounds, in particular tetraalkyl and tetraalkoxy-metals, can also be used. More precisely, the following compounds are preferred: Stannous or stannic chloride for tin, germanium tetrachloride for germanium, lead nitrate for lead. For all these salts, a strongly acid solution of pH lower than about 3 and preferably lower than about 1 will be preferred to a mere aqueous solution. The solution acidifying agent may be an organic or inorganic acid. Examples of acids are hydrochloric acid, nitric acid, oxalic acid, malonic acid, citric acid, malic acid, formic acid and tartaric acid.

When the matrix is impregnated with an organometallic compound of a group IVA metal, the preferred compounds are tetrabutyltin, tetramethyltin diphenyltin, tetrapropylgermanium and tetraethyllead.

After impregnation with the group IVA metal, the group VIII metal is for example introduced by means of a solution of at least one compound of said group VIII metal. When the group VIII metal is platinum, a solution of hexachloroplatinic acid will be preferably used; platinum will then deposit on the matrix by anion exchange. It is also possible to use the so-called dry impregnation technique.

The matrix on which the one or more metals of group IVA and the one or more metals of group VIII have been deposited is then intimately admixed with a mordenite having the above-described characteristics and particular morphology; then the mixture is shaped by any means known in the art such for example as extrusion, pelletizing or bowl granulation. The product is then dried and generally roasted at about 300°–600° C.

Another preferred method for preparing the catalyst according to the invention consists of introducing the group VIII metal only after having intimately admixed with mordenite the matrix impregnated with the group IVA metal. The group VIII metal is then introduced either before or after the shaping step. A group VIII metal compound will be used to deposit said metal, in major part on the matrix. Advantageously a solution of an inorganic compound of said metal will be used. For platinum, said compound will be preferably hexachloroplatinic acid.

When the metals are introduced on mordenite, a first metal of group IVA is preferably introduced by any method known in the art and preferably by impregnation with a solution of one of the metal salts, preferably of the above-mentioned salts, particularly the organometallic compounds of said metals and then the group VIII metal is introduced. The mordenite containing group IVA and group VIII metals is intimately admixed with the matrix and then the mixture is shaped, dried and usually roasted, for example at a temperature from 300° to 600° C.

Another preferred method consists of only introducing the group IVA metal on the mordenite, admixing the resultant product with the matrix and then introducing the group VIII metal, optionally after shaping, by means of a compound of said metal so that said metal be deposited, in major part, on the mordenite. A solution of organic complex of said metal is then advantageously used. Preferably platinum tetrammine will be used to deposit platinum on mordenite by cation exchange. If necessary, the resultant product is shaped, then dried and usually roasted at a temperature from 300° to 600° C.

The group VIII metal may also be first deposited on the matrix, for example, when platinum is concerned, by anion exchange with hexachloroplatinic acid, or on mordenite, for example by cation exchange with a tetrammine platinum salt. The two obtained products may then be:
either directly impregnated with the group IVA metal according to the above-described methods and then respectively admixed with the mordenite and with the binder and shaped by any method known in the art,
or admixed with mordenite and the binder respectively and then shaped. The group IVA metal will then be deposited on the shaped product by any one of the above-described methods.

It is also possible to admix the matrix with the mordenite, to shape them and then to deposit the group VIII metal by anion or cation exchange. The group IVA metal, for example tin, will then be deposited on the resultant product by any one of the above-described methods.

Irrespective of the method used to deposit the group IVA metal, this metal must be preferably present in the final catalyst at a higher oxidation state than that of the element metal. For tin, this means that the best results are obtained when substantially all the tin is at an oxidation state of +2 or +4 and by example in the form of tin oxide.

The use of the catalysts according to the invention, preferably prepared according to one of the above-described methods, containing the specified proportion of each of the elements and containing the mordenite of particular morphology (needles) and characteristics, results in a substantial increase of activity and selectivity in the hydroisomerization reaction of cuts containing a high proportion of normal paraffins having 4 to 7 carbon atoms per molecule, as compared with the hydroisomerization catalysts of the prior art.

The catalyst according to the invention, prepared according to one of the above-described methods, may be used to isomerize n-paraffins having 4, 5, 6 or 7 carbon atoms per molecule, particularly n-paraffins with 5 or 6 carbon atoms per molecule, in the following conditions.

According to the invention, the charge containing a high proportion of light paraffins having 5 or 6 carbon atoms and hydrogen are contacted with a catalyst of the above-described type, under isomerization conditions. The contact may be performed by using the catalyst in fixed bed, in fluidized bed or in batch (i.e. in discontinuous operation).

The process is conducted between 200° and 300° C., preferably between 250° and 280° C., at $H_2$ partial pressures ranging from the atmospheric pressure to 70 bars (7 MPa) and preferably from 5 to 50 bars (0.5 to 5 MPa). The space velocity may range from 0.5 to 10 liters of liquid hydrocarbons per liter of catalyst and per hour, preferably 1 to 5. The $H_2$/charge molar ratio may vary within wide limits and is usually from 0.5 to 10, preferably from 1 to 5. The isomerization being a balanced reaction, the isomerizate still contains a substantial amount of unconverted n-paraffins. These paraffins may be separated from the isomers, for example by distillation or fractionation over molecular sieve and recycled to the isomerization unit.

EXAMPLES

The following examples are given to further illustrate the invention and must not be considered as limiting the scope thereof.

The performances are expressed in terms of n-alkane (n-hexane or n-butane) conversion and of isomerization selectivity and cracking selectivity, defined as follows:

$$\text{Conversion} = \frac{((\text{n-alkane input weight}) - (\text{n-alkane output weight})) \times 100}{\text{n-alkane input weight}}$$

$$\text{Isomerization selectivity} = \frac{\Sigma(\text{weight of isomers}) \times 100}{\Sigma(\text{weight of the reaction products})}$$

$$\text{Cracking selectivity} = \frac{\Sigma(\text{weight of } C_1\text{-}C_5 \text{ (or } C_1\text{-}C_3) \text{ products}) \times 100}{\Sigma(\text{weight of the reaction products})}$$

EXAMPLE 1

Preparation of Catalyst A

The alumina used as shaping binder is an alumina gel available on the market as powder and having a specific surface of 250 m²/g and a pore volume of 0.7 cm³/g.

On said alumina, 0.8% of tin are then deposited from a solution of tin chloride, acidified with a decanormal hydrochloric acid solution. The impregnated alumina is then dried for a night in a stove at 120° C., then intimately admixed with a mordenite pretreated according to the above-described technique, recalled hereinafter.

The raw material is a so-called small-pore mordenite, referenced Alite 150, from Society Chimique de la Grande Paroisse. Its chemical formula in anhydrous state is: $Na\ AlO_2(SiO_2)_{5.5}$ and its benzene adsorption capacity is 1% by weight in proportion to the weight of dry solid unit cell volume: 2.79 nm³; sodium content: 5.3% by weight, kinetic diameter of the adsorbed molecules: $3.8 \times 10^{-10}$ m); 50 g of said powder are dipped into a 2M ammonium nitrate solution and the suspension is brought to 95° C. for 2 hours.

The involved volume of ammonium nitrate solution is 4 times the weight of dry mordenite (V/P=4). This cation exchange operation is repeated 3 times. After the 3rd exchange, the product is washed with water at 20° C. for 20 minutes with a V/P ratio of 4. The sodium content, expressed in percent of the dry weight, decreases from 5.3 to 0.1%. The product is then filtered and subjected to roasting in confined atmosphere (self steaming) at 600° C. for 2 hours.

Then an acid etching is performed with 0.58N hydrochloric acid, by bringing the product to reflux in the hydrochloric aqueous solution at 90° C. for 2 hours with a V/P ratio of 8. The product is then filtered, washed with 0.1N hydrochloric acid and then with water.

The Si/Al atomic ratio of said mordenite is equal to 12, its unit cell volume to 2.750 nm³, its sodium content to 300 ppm, its benzene adsorption capacity to 9.6% by weight with respect to the weight of dry solid and the kinetic diameter of the adsorbed molecules is $6.8\ 10^{-10}$ m. Said mordenite has a needle morphology with needles of 5 μm average length having hexagonal faces of about 1 μm length and about 0.3 μm height.

After mixing, the mixture, consisting of 25% of alumina impregnated with tin and 75% of mordenite, is forced through a drawing plate. The formed extrudates, of 1.2 mm diameter, are then dried and roasted. 0.4% of platinum are then deposited on this carrier by anion exchange from a solution of hexachloroplatinic acid. The extrudates are then dried in a stove at 120° C. and roasted in dry air at 500° C. The resultant catalyst contains, by weight: 24.7% of alumina, 74.7% of mordenite, 0.20% of tin and 0.4% of platinum.

This catalyst is charged as fixed bed in a catalytic unit and reduced in hydrogen at 450° C. It is then tested with a charge of normal hexane in the following conditions: temperature: 270° C., pressure: 30 bars (3 MPa), n-hexane weight per mordenite weight unit and per hour: 2, molar ratio of hydrogen to normal hexane: 4. The performances indicated in Table I are obtained after 30 hours of catalyst operation.

EXAMPLE 2

Preparation of Catalyst B

Catalyst B differs from catalyst A in that tin is deposited on the mordenite with tetramethyltin as precursor.

Mordenite is brought to reflux in a solution of heptane containing a tetramethyltin amount corresponding to 0.5% by weight of tin, rinsed with heptane and dried. It is then intimately admixed with peptized alumina. After mixing, the mixture is forced through a drawing plate. The resultant extrudates are dried and roasted.

0.4% of platinum are deposited on the extrudates by cation exchange with tetramine platinum chloride $Pt(NH_3)_4Cl_2$. The catalytic performances are reported in Table I.

EXAMPLE 3

Preparation of Catalyst C

Catalyst C differs from catalyst A described in example 1 in that, instead of tin, 0.8% of germanium are deposited on the alumina by means of germanium tetrachloride. The subsequent steps are strictly similar to those described in example 1. The performances are given in Table I.

EXAMPLE 4

Preparation of Catalyst D

Catalyst D differs from catalyst A described in example 1 in that, instead of tin, 0.8% of lead are deposited on the alumina by means of lead nitrate. The subsequent steps are strictly similar to those described in example 1. The performances are given in Table I.

EXAMPLE 5

Preparation of Catalyst E (Comparison)

The mordenite used for preparing catalyst E is obtained from the same initial mordenite as that used in example 1; this product is just exchanged 4 times with 2M ammonium nitrate solutions but is not subjected to acid or thermal treatments. The Si/Al ratio is equal to 5.5, the sodium content is 300 ppm, the unit cell volume 2.778 nm$^3$ and the capacity of benzene adsorption 1.2% by weight. The catalyst is prepared as in example 1; it contains by weight the same alumina, mordenite, tin and platinum amounts as the catalyst obtained in example 1. The performances, summarized in Table I, show that, as a result of the clogged structure of mordenite (it only adsorbs 1.2% by weight of benzene) the isomerization activity is low.

EXAMPLE 6

The catalyst A, prepared according to the invention, was also tested with normal butane in the following conditions: temperature: 350° C., pressure: 30 bars (3 MPa), normal butane weight per mordenite weight unit and per hour: 1.2, hydrogen to normal butane molar ratio: 4. The performances of this catalyst after 30 hours of operation are the following:
n-butane conversion rate: 80%
isomerization selectivity: 99.5%
cracking selectivity: 0.5%

EXAMPLE 7

Preparation of Catalyst F According to the Invention

After mixing and shaping of the peptized matrix (alumina and mordenite previously subjected to a pretreatment whose characteristics are described in example 1), 0.5% of platinum is deposited thereon from a solution of tetramine platinum complex, so that platinum be preferentially deposited on mordenite. After roasting and reduction of the metal phase, 0.5% of tin are deposited while bringing the catalyst to reflux in a solution of tetrabutyl tin in heptane. After drying, the catalyst is reduced in situ. The performances are reported in Table I.

The performances indicated in Table I for catalysts A to D and F according to the invention are clearly higher than those obtained with the comparison catalyst E.

EXAMPLE 8

Preparation of Catalyst G (Comparison)

Catalyst G differs from catalyst B described in example 11 by the use of a wide-pore mordenite, as powder, referenced Zeolon 100 Na, produced by NORTON Company.

50 g of this powder are brought to reflux for 2 hours at 950° C. in an ammonium nitrate solution. This exchange is repeated twice. After the last exchange, the product is washed with water for 20 mn at 20° C., filtered and roasted in confined atmosphere (self steaming) at 600° C. for 2 hours. The thermal treatment is followed by an acid etching with 0.58N hydrochloric acid. The solid is brought to reflux in a hydrochloric acid aqueous solution at 90° C. for 2 hours and then washed with water.

The Si/Al atomic ratio of the resultant zeolite is equal to 12, its mesh volume to 2.752 nm$^3$ and its sodium content to 250 ppm. This product, contrary to the mordenite according to the invention, has not a needle morphology.

The resultant mordenite is brought to reflux in a solution of heptane containing a tetramethyl tin amount corresponding to 0.5% by weight of tin, rinsed with heptane and dried. It is then intimately admixed with the peptized alumina. After mixing, the mixture is forced through a drawing plate. The resultant extrudates are dried and roasted.

0.4% of platinum is deposited on this carrier by cation exchange with tetramine platinum chloride Pt(NH$_3$)$_4$Cl$_2$. The catalytic performances are reported in Table I.

TABLE I

| EXAMPLE | CATALYST | CONVERSION % | ISOMERIZATION SELECTIVITY % | CRACKING SELECTIVITY % |
|---|---|---|---|---|
| 1 | A | 80 | 99.5 | 0.5 |
| 2 | B | 80 | 99.8 | 0.2 |
| 3 | C | 80 | 99.3 | 0.7 |
| 4 | D | 80 | 99.3 | 0.7 |
| 5 | E | 10 | 97.0 | 3 |
| 7 | F | 80 | 99.7 | 0.3 |
| 8 | G | 57 | 97.5 | 2.5 |

What is claimed as the invention is:

1. A catalyst containing by weight:
  (a) from 10 to 99.99% of a mordenite adsorbing molecules of a kinetic diameter larger than about $6.6 \times 10^{-10}$ m, having a Si/Al atomic ratio from about 5 to 50, a sodium content by weight lower than 0.2% of the total weight of dry mordenite, a volume V of a unit cell from 2.73 to 2.78 cubic nanometers, a benzene adsorption capacity of more than 5% by weight with respect to the dry mordenite weight, said mordenite being in major part shaped as needles,
  (b) from 0 to 89.99% of a matrix selected from the group consisting of alumina, silica, magnesia, zirconia, natural clays or mixtures thereof,
  (c) from 0.005 to 15% of at least one metal from group VIII of the periodic classification of elements, and
  (d) from 0.005 to 10% of at least one metal from group IVA of the periodic classification, selected from the group consisting of tin, germanium and lead.

2. A catalyst according to claim 1, wherein the mordenite has the capacity to adsorb molecules of a kinetic diameter larger than about $6.6 \times 10^{-10}$ m, has a Si/Al atomic ratio from about 5 to 30, a sodium content by weight lower than 0.1% by weight of the total dry mordenite weight, a volume of the unit cell from 2.74 to 2.77 cubic nanometers, a benzene adsorption capacity higher than 8% of the dry mordenite weight, said mordenite being in major part shaped as needles of 2 to 20 $\mu$m length having hexagonal faces of 0.5 to 4 $\mu$m length and of 0.1 to 2 $\mu$m height.

3. A catalyst according to claim 1, characterized by a content by weight of:
(a) 35–85% of mordenite,
(b) 15–60% of matrix,
(c) 0.05–10% of at least one group VIII metal,
(d) 0.01–5% of at least one group IVA metal.

4. A catalyst according to claim 1, wherein the group VIII metal is selected from the group consisting of platinum, palladium and nickel, the platinum or palladium content being from 0.05 to 1% by weight and the nickel content from 0.1 to 10% by weight.

5. A catalyst according to claim 1, wherein the group IVA metal is tin.

6. A catalyst according to claim 1, wherein the matrix is alumina.

* * * * *